US 9,772,276 B2

(12) United States Patent
Fujimoto

(10) Patent No.: US 9,772,276 B2
(45) Date of Patent: Sep. 26, 2017

(54) DETECTION DEVICE AND PRODUCTION METHOD FOR SAME

(71) Applicant: Konica Minolta, Inc., Tokyo (JP)

(72) Inventor: Akihiro Fujimoto, Tokyo (JP)

(73) Assignee: KONICA MINOLTA, INC., Tokyo (JP)

(*) Notice: Subject to any disclaimer, the term of this patent is extended or adjusted under 35 U.S.C. 154(b) by 0 days.

(21) Appl. No.: 15/304,359

(22) PCT Filed: May 13, 2015

(86) PCT No.: PCT/JP2015/063802
§ 371 (c)(1),
(2) Date: Oct. 14, 2016

(87) PCT Pub. No.: WO2015/174463
PCT Pub. Date: Nov. 19, 2015

(65) Prior Publication Data
US 2017/0038296 A1 Feb. 9, 2017

(30) Foreign Application Priority Data
May 14, 2014 (JP) ................. 2014-100320

(51) Int. Cl.
G01N 21/35 (2014.01)
G01N 21/3581 (2014.01)
G01N 21/3586 (2014.01)

(52) U.S. Cl.
CPC ..... *G01N 21/3581* (2013.01); *G01N 21/3586* (2013.01); *G01N 2201/061* (2013.01); *G01N 2201/066* (2013.01)

(58) Field of Classification Search
CPC .......... G01N 21/3581; G01N 21/3586; G01N 2201/066; G01N 2201/061
(Continued)

(56) References Cited

U.S. PATENT DOCUMENTS

2012/0097978 A1* 4/2012 Ouchi ................... G01J 3/0256
257/77
2012/0318983 A1* 12/2012 Ouchi ................ G01N 21/3586
250/339.11
(Continued)

FOREIGN PATENT DOCUMENTS

JP 2004354246 A 12/2004
JP 2006184078 A 7/2006
(Continued)

OTHER PUBLICATIONS

International Search Report dated Aug. 18, 2015 for PCT/JP2015/063802 and English translation.
Written Opinion dated Aug. 18, 2015 for PCT/JP2015/063802.

Primary Examiner — Marcus Taningco
Assistant Examiner — Gisselle Gutierrez
(74) Attorney, Agent, or Firm — Lucas & Mercanti, LLP

(57) ABSTRACT

A detection device having: a terahertz wave generation element; a terahertz wave detection element; a first transmission path arranged upon the terahertz wave generation element; a second transmission path arranged upon the terahertz wave detection element; and a sealed section arranged between the terahertz wave generation element and the terahertz wave detection element and separated from the first transmission path and the second transmission path, so as to surround the first transmission path and the second transmission path. A space between an emission surface in the first transmission path and an incident surface in the second transmission path is connected to a space between the first transmission path and the sealed section and to a space between the second transmission path and the sealed section.

19 Claims, 11 Drawing Sheets

(58) Field of Classification Search
USPC .................................................... 250/341.1
See application file for complete search history.

(56) References Cited

U.S. PATENT DOCUMENTS

| | | | |
|---|---|---|---|
| 2016/0116402 A1* | 4/2016 | Chen .................. | G01N 21/3581 250/343 |
| 2016/0377958 A1* | 12/2016 | Ouchi .................. | G02F 1/0123 250/353 |
| 2017/0074789 A1* | 3/2017 | Ataka ................ | G01N 21/3581 |

FOREIGN PATENT DOCUMENTS

| | | |
|---|---|---|
| JP | 2006275592 A | 10/2006 |
| JP | 2007309858 A | 11/2007 |
| JP | 2008224449 A | 9/2008 |
| JP | 2008224451 A | 9/2008 |

\* cited by examiner

DETECTION DEVICE AND PRODUCTION METHOD FOR SAME

CROSS REFERENCE TO RELATED APPLICATION

This Application is a 371of PCT/JP2015/063802filed on May 13, 2015, which, in turn, claimed the priority of Japanese Patent Application No. JP 2014-100320 filed May 14, 2014, both applications are incorporated herein by reference.

TECHNICAL FIELD

The present invention relates to a detection device for acquiring information of an object by detecting the state of terahertz waves having passed through the object, and a method of manufacturing the detection device.

BACKGROUND ART

Terahertz waves consist of electromagnetic waves having a frequency of about 0.01 to 100 THz between light waves and radio waves, and have an intermediate property between light waves and radio waves. In recent years, techniques of acquiring information of an object by detecting terahertz waves having passed through the object or by detecting the state of terahertz waves reflected by the object have been proposed (see, for example, PTLS 1 to 3).

PTL 1 discloses a reflection type detection apparatus which acquires information of an object by detecting the state of terahertz waves reflected by the object. The detection apparatus disclosed in PTL 1 includes a terahertz wave generation section, a prism and a terahertz wave detection section. The terahertz wave generation section applies femtosecond pulse laser light to InAs to generate terahertz waves. The terahertz waves are incident on the prism through a light path including two off-axis parabolic mirrors. The object is placed on a planar surface of the prism. When totally reflected by the planar surface under the object, the terahertz waves incident on the prism become terahertz waves containing the information of the object. The terahertz waves containing the information of the object are emitted from the prism, and reach the terahertz wave detection section through the light path including the two off-axis parabolic mirrors. The terahertz wave detection section detects the terahertz waves containing the information of the object.

In the detection apparatus disclosed in PTL 1, a large number of optical elements are provided between the terahertz wave generation section and the prism, and between the prism and the terahertz wave detection section. As such, the detection apparatus disclosed in PTL 1 has a problem that the device size is large. In addition, since terahertz waves are absorbed by the moisture in the air, the space between the terahertz wave generation section and the prism and the space between the prism and the terahertz wave detection section are required to be filled with nitrogen, or vacuumized. To solve such problems, PTL 2 proposes a technique in which the terahertz wave generation element and the terahertz wave detection element are integrated with the prism.

PTL 2 discloses a reflection type detection apparatus which acquires the information of an object by detecting the state of the terahertz waves reflected by the object and a reflection type detection device used for the reflection type detection apparatus. The detection apparatus disclosed in PTL 2 includes a light source, a detection device, and a light detector. The detection device includes a prism, a terahertz wave generation element disposed on the incidence surface of the prism, and a terahertz wave detection element disposed on the emission surface of the prism. The light source applies femtosecond pulse laser light to the terahertz wave generation element of the detection device. As a result, terahertz waves are generated at the terahertz wave generation element, and the terahertz waves travel in the prism. The object is placed on the planar surface of the prism. When totally reflected by the planar surface under the object, the terahertz waves incident on the prism become terahertz waves containing the information of the object, and reach the terahertz wave detection element. The terahertz wave detection element generates light containing information of the object in accordance with the input terahertz waves. The light detector detects the light containing the information of the object.

In addition, PTL 3 discloses a transmission type detection device which acquires information of an object by detecting the state of the terahertz waves having passed through the object. FIG. 1 is a perspective view of the detection device disclosed in PTL 3. As illustrated in FIG. 1, detection device 10 disclosed in PTL 3 includes two metal plates 12a and 12b, two polystyrene plates 14a and 14b and two photoconductive antennas 16a and 16b. Two metal plates 12a and 12b are disposed to face each other with a distance of approximately 100 μm therebetween, and two polystyrene plates 14a and 14b are disposed between metal plates 12a and 12b. The laminated body composed of two metal plates 12a and 12b and two polystyrene plates 14a and 14b serves as a parallel flat plate waveguide path. Space 18 for housing an object is formed between two polystyrene plates 14a and 14b. The distance between two polystyrene plates 14a and 14b is approximately 50 μm. The object housed in space 18 is thus present at a middle point of the waveguide path. Photoconductive antenna 16a is disposed at one end portion of the laminated body, and photoconductive antenna 16b is disposed at the other end portion of the laminated body. When femtosecond pulse laser light is applied to photoconductive antenna 16a, terahertz waves are generated. The terahertz waves travel through polystyrene plate 14a, space 18 (object) and polystyrene plate 14b, and reach photoconductive antenna 16b. Photoconductive antenna 16b detects the terahertz waves transmitted through the object (converts the terahertz waves into an electric signal).

Since attenuation of terahertz waves is large, and terahertz waves are difficult to be directly applied to polystyrene plate 14a, detection device 10 disclosed in PTL 3 applies laser light to photoconductive antenna 16a to generate terahertz waves. In addition, since terahertz waves are attenuated when the size of space 18 is increased, the size of space 18 is preferably small as much as possible.

Even with a small size, detection device 10 disclosed in PTL 3 can detect the state of the terahertz waves having passed through the object.

CITATION LIST

Patent Literature

PTL 1
Japanese Patent Application Laid-Open No. 2004-354246
PTL 2
Japanese Patent Application Laid-Open No. 2008-224449
PTL 3
Japanese Patent Application Laid-Open No. 2006-184078

SUMMARY OF INVENTION

Technical Problem

When the terahertz waves having passed through the object in space 18 have to be efficiently detected with transmission type detection device 10 disclosed in PTL 3, the distance between two polystyrene plates 14a and 14b has to be extremely reduced, and consequently the size of space 18 for housing an object is extremely reduced. When space 18 has such a small size, it is difficult to install an object in space 18, and it is difficult to cause a reaction between the object and another material in space 18.

An object of the present invention is to provide a transmission type detection device which acquires information of an object by detecting the state of the terahertz waves having passed through the object, and can achieve downsizing and detection with high sensitivity while sufficiently ensuring a space for housing an object, and a manufacturing method of the transmission type detection device.

Solution to Problem

To solve the above-mentioned problems, a detection device according to embodiments of the present invention is a detection device for acquiring information of an object by detecting a state of terahertz waves having passed through the object, the detection device including: a terahertz wave generation element; a terahertz wave detection element disposed to face the terahertz wave generation element; a first transmission path disposed on the terahertz wave generation element to protrude from the terahertz wave generation element toward the terahertz wave detection element; a second transmission path disposed on the terahertz wave detection element to protrude from the terahertz wave detection element toward the terahertz wave generation element; and a sealing part disposed between the terahertz wave generation element and the terahertz wave detection element to surround the first transmission path and the second transmission path, the sealing part being separated from the first transmission path and the second transmission path. The first transmission path includes an emission surface which emits terahertz waves generated at the terahertz wave generation element, the emission surface being disposed at an end of the first transmission path; the second transmission path includes an incidence surface on which the terahertz waves emitted from the emission surface are incident, the incidence surface being disposed at an end of the second transmission path to face the emission surface, the incidence surface being separated from the emission surface; and a space between the emission surface and the incidence surface is communicated with a space between the first transmission path and the sealing part and a space between the second transmission path and the sealing part.

To solve the above-mentioned problems a method of manufacturing the detection device according to embodiments of the present invention includes: forming a plurality of pairs of first electrode films on a first surface of a first photoconductive substrate; forming a plurality of pairs of second electrode films on a first surface of a second photoconductive substrate; forming a plurality of first transmission paths on a second surface of the first photoconductive substrate; forming a plurality of second transmission paths on a second surface of the second photoconductive substrate; producing a laminated body by disposing a sealing sheet including a plurality of through holes for housing the first transmission path and the second transmission path at a position between the second surface of the first photoconductive substrate and the second surface of the second photoconductive substrate, and by fixing the first photoconductive substrate, the sealing sheet and the second photoconductive substrate; and obtaining a plurality of detection devices by cutting the laminated body at a position between the through holes.

Advantageous Effects of Invention

In the present invention, the sealing part is provided between the terahertz wave generation element and the terahertz wave detection element to surround the first transmission path and the second transmission path such that a space for housing an object is sufficiently ensured in the sealing part. Consequently, even when the distance between the first transmission path and the second transmission path is reduced, the object can be easily move to the position between the first transmission path and the second transmission path, and thus it is possible to provide a detection device which can achieve downsizing and detection with high sensitivity. With the detection device according to the embodiments of the present invention, the state of the terahertz waves having passed through the object can be detected with high sensitivity.

DESCRIPTION OF EMBODIMENTS

Embodiments of the present invention are described below in detail with reference to the accompanying drawings.

[Embodiment 1]

(Configuration of Detection Device)

Figure 1:
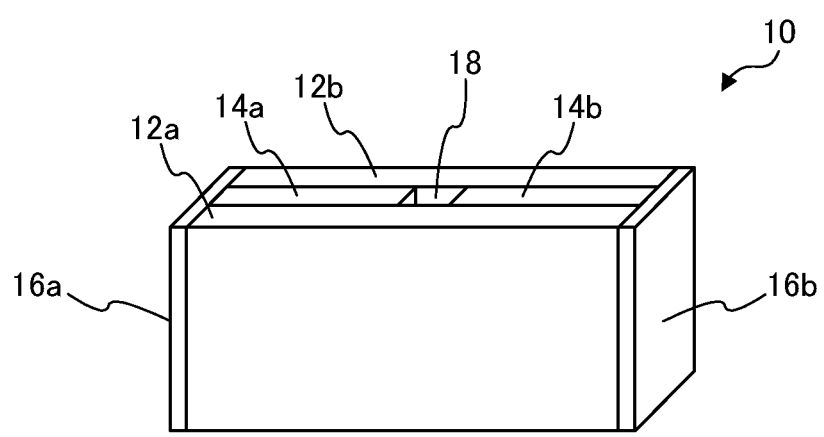
FIG. 1 is a perspective view of a transmission type detection device disclosed in PTL 3.
Figure 2A:
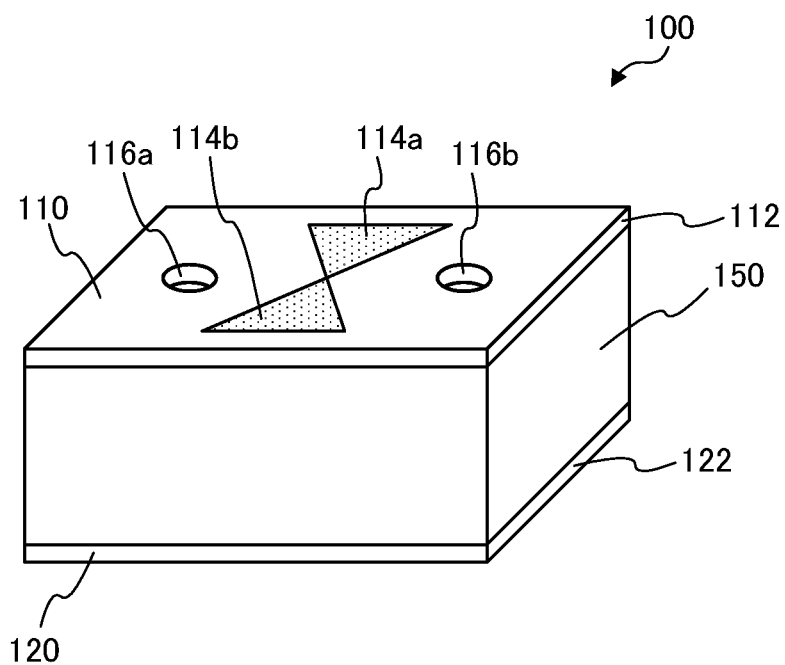
FIG. 2A is a perspective view of a detection device according to Embodiment 1.
Figure 2B:
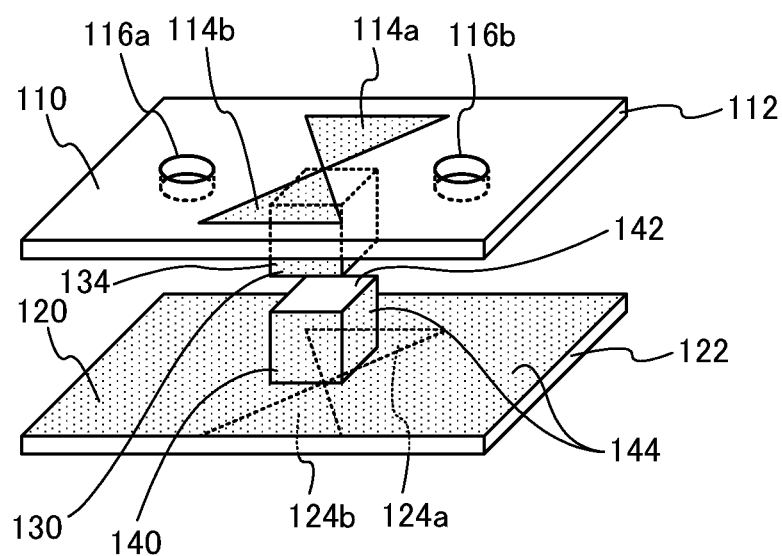
FIG. 2B is a perspective view of the detection device according to Embodiment 1 in which a sealing part is omitted.
Figure 3:
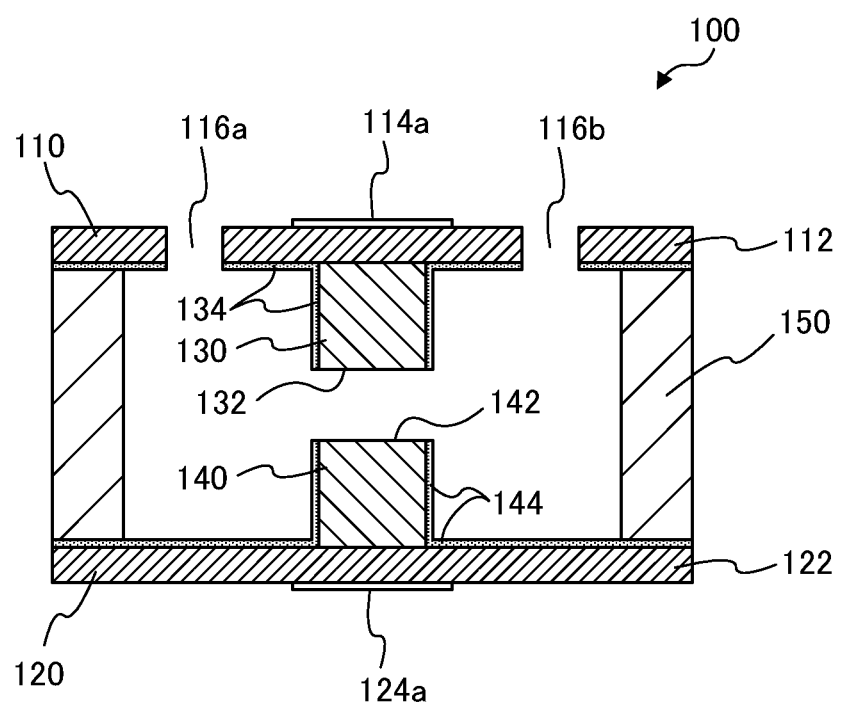
FIG. 3 is a sectional view of the detection device according to Embodiment 1.

FIG. 2 and FIG. 3 illustrate detection device 100 according to Embodiment 1 of the present invention. FIG. 2A is a perspective view of detection device 100, and FIG. 2B is a perspective view of detection device 100 in which sealing part 150 is omitted. FIG. 3 is a sectional view of detection device 100.

Detection device 100 is a device (chip) for acquiring information of an object by detecting the state of terahertz waves having passed through the object. Here, the "terahertz wave" is electromagnetic waves whose frequency is within a range of 0.01 to 100 THz. While the kind of the object is not limited, detection device 100 according to the present embodiment is particularly effective for objects having fluidity such as liquid and powder.

As illustrated in FIG. 2 and FIG. 3, detection device 100 includes terahertz wave generation element 110, terahertz wave detection element 120, first waveguide path 130, second waveguide path 140 and sealing part 150.

Terahertz wave generation element 110 generates terahertz waves for transmission through an object. In the present embodiment, terahertz wave generation element 110 is a photoconductive antenna including photoconductive substrate 112, and a pair of electrode films 114a and 114b disposed on photoconductive substrate 112 (for example, low-temperature growth GaAs). However, the type of terahertz wave generation element 110 is not limited as long as desired terahertz waves can be generated. Examples of terahertz wave generation element 110 include a nonlinear optical crystal (for example, ZnTe).

Terahertz wave detection element 120 is disposed to face terahertz wave generation element 110. Terahertz wave detection element 120 detects terahertz waves having passed through the object after being emitted from terahertz wave generation element 110. In the present embodiment, terahertz wave detection element 120 is a photoconductive antenna including photoconductive substrate 122, and a pair of electrode films 124a and 124b disposed on photoconductive substrate 122 (for example, low-temperature growth GaAs). As with terahertz wave generation element 110, the type of terahertz wave detection element 120 is not limited as long as terahertz waves emitted from terahertz wave generation element 110 can be detected. Examples of terahertz wave detection element 120 include a nonlinear optical crystal (for example, ZnTe).

First waveguide path 130 is a transmission path disposed on terahertz wave generation element 110 (photoconductive substrate 112). To be more specific, first waveguide path 130 is disposed at a position (in the present embodiment, the rear side of the gap of the pair of electrode films 114a and 114b) corresponding to a portion where terahertz waves are generated in terahertz wave generation element 110. First waveguide path 130 protrudes from terahertz wave generation element 110 (photoconductive substrate 112) toward terahertz wave detection element 120, and includes, at an end thereof, emission surface 132 that emits terahertz waves. First waveguide path 130 transmits the terahertz waves generated at terahertz wave generation element 110 to emission surface 132, and emits the terahertz waves from emission surface 132.

Second waveguide path 140 is a transmission path disposed on terahertz wave detection element 120 (photoconductive substrate 122). To be more specific, second waveguide path 140 is disposed at a position (in the present embodiment, the rear side of the gap of the pair of electrode films 124a and 124b) corresponding to a portion where terahertz waves are detected at terahertz wave detection element 120. Second waveguide path 140 protrudes from terahertz wave detection element 120 (photoconductive substrate 122) toward terahertz wave generation element 110, and includes, at an end thereof, incidence surface 142 on which terahertz waves emitted from emission surface 132 of first waveguide path 130 are incident. Emission surface 132 and incidence surface 142 are separated from each other to face each other. Detection device 100 of the present embodiment irradiates an object which is present between emission surface 132 and incidence surface 142 with terahertz waves to detect the terahertz waves having passed through the object. The terahertz waves having passed through the object are incident on second waveguide path 140, and second waveguide path 140 transmits the terahertz waves to terahertz wave detection element 120.

The type of the material of first waveguide path 130 and second waveguide path 140 is not limited as long as absorption (loss) and dispersion of terahertz waves are small. Examples of the material of first waveguide path 130 and second waveguide path 140 include resins (for example, polytetrafluoroethylene), ceramics, and silicon. The material of first waveguide path 130 and the material of second waveguide path 140 may be different from each other. Preferably, first waveguide path 130 and second waveguide path 140 are made of a resin material from the standpoint of the ease of working.

The shape of first waveguide path 130 and second waveguide path 140 is not limited as long as terahertz waves can be efficiently transmitted. In the present embodiment, each of first waveguide path 130 and second waveguide path 140 has a cuboid shape.

While the length of first waveguide path 130 (the height from terahertz wave generation element 110) and the length of second waveguide path 140 (the height of terahertz wave detection element 120) are not limited, the lengths are preferably each 10 μm or greater. When each of first waveguide path 130 and second waveguide path 140 has a length of 10 μm or greater, the influence of multiple reflection can be reduced by delaying the travelling of the stray light. From the standpoint of the handleability of detection device 100, the upper limit of the length of first waveguide path 130 and second waveguide path 140 is about several millimeters.

The widths of first waveguide path 130 and second waveguide path 140 (the lengths in the direction parallel to emission surface 132 and incidence surface 142) are not limited, and may be appropriately selected in accordance with the wavelength of terahertz waves. By setting the widths of first waveguide path 130 and second waveguide path 140 in accordance with the wavelength of terahertz waves, the S/N ratio can be improved by intensifying terahertz waves of a desired wavelength.

The distance between emission surface 132 and incidence surface 142 is not limited. In terms of the balance between the movability of the object and the loss of terahertz waves, the distance between emission surface 132 and incidence surface 142 preferably falls within a range of 10 to 100 μm.

The side surface of first waveguide path 130 (the surface other than emission surface 132) and the side surface of second waveguide path 140 (the surface other than incidence surface 142) are preferably covered with metal films 134 and 144 for reflecting terahertz waves. In the present embodiment, the rear surface of terahertz wave generation element 110 (photoconductive substrate 112) and the side surface of first waveguide path 130 are covered with metal film 134 for reflecting terahertz waves. In addition, the rear surface of terahertz wave detection element 120 (photoconductive substrate 122) and the side surface of second waveguide path 140 are covered with metal film 144 for reflecting terahertz waves. No metal film 134 is present at the interface between terahertz wave generation element 110 (photoconductive substrate 112) and first waveguide path 130, and no metal film 144 is present at the interface between terahertz wave detection element 120 (photoconductive substrate 122) and second waveguide path 140. The type of the metal of metal films 134 and 144 is not limited as long as terahertz waves can be reflected. Examples of the metal of metal films 134 and 144 include gold, silver, aluminum, and alloys thereof.

Figure 4:
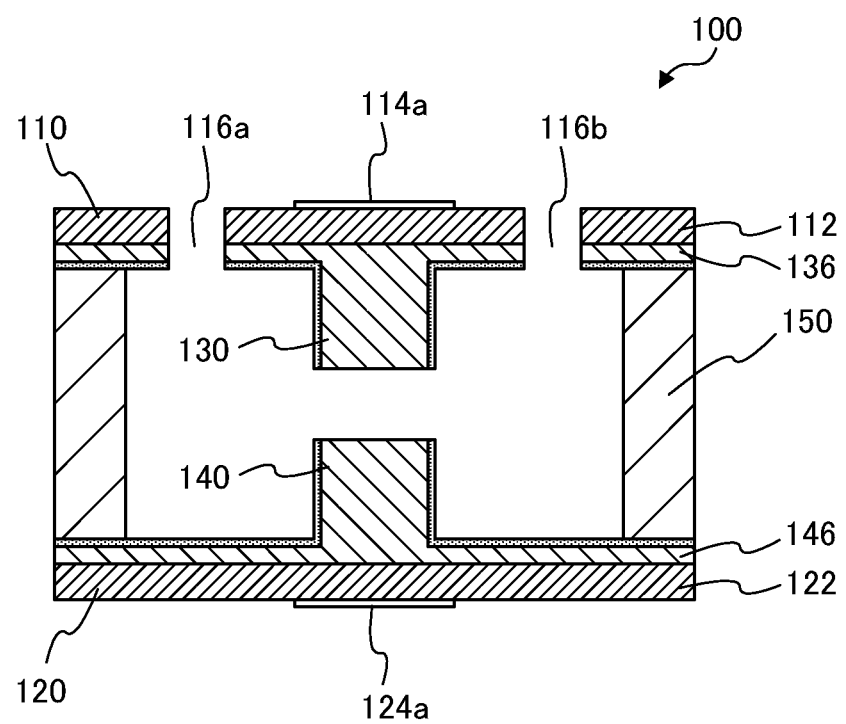
FIG. 4 is a sectional view of a modification of the detection device according to Embodiment 1.

It is to be noted that, from the viewpoint of the ease of manufacturing, first waveguide path 130 may be formed integrally with base 136 disposed on the rear surface of terahertz wave generation element 110 (photoconductive substrate 112) as illustrated in FIG. 4. Likewise, second waveguide path 140 may be formed integrally with base 146 disposed the rear surface of terahertz wave detection element 120 (photoconductive substrate 122).

Sealing part 150 is disposed between terahertz wave generation element 110 (photoconductive substrate 112) and terahertz wave detection element 120 (photoconductive substrate 122) to surround first waveguide path 130 and second waveguide path 140. In addition, sealing part 150 is separated from first waveguide path 130 and second waveguide path 140, and thus a space for housing an object, which is surrounded by terahertz wave generation element 110 (photoconductive substrate 112), terahertz wave detection element 120 (photoconductive substrate 122) and sealing part 150, is formed around first waveguide path 130 and second waveguide path 140. For the purpose of housing an object in this space, terahertz wave generation element 110 (photoconductive substrate 112) is provided with two through holes 116a and 116b.

As described above, an object to be irradiated with terahertz wave is required to be present in the space between emission surface 132 and incidence surface 142, and the space between emission surface 132 and incidence surface 142 is communicated with the space around first waveguide path 130 and second waveguide path 140 (the space between first waveguide path 130 and sealing part 150, and the space between second waveguide path 140 and sealing part 150). Thus, the object can freely move in the spaces.

Figure 5:
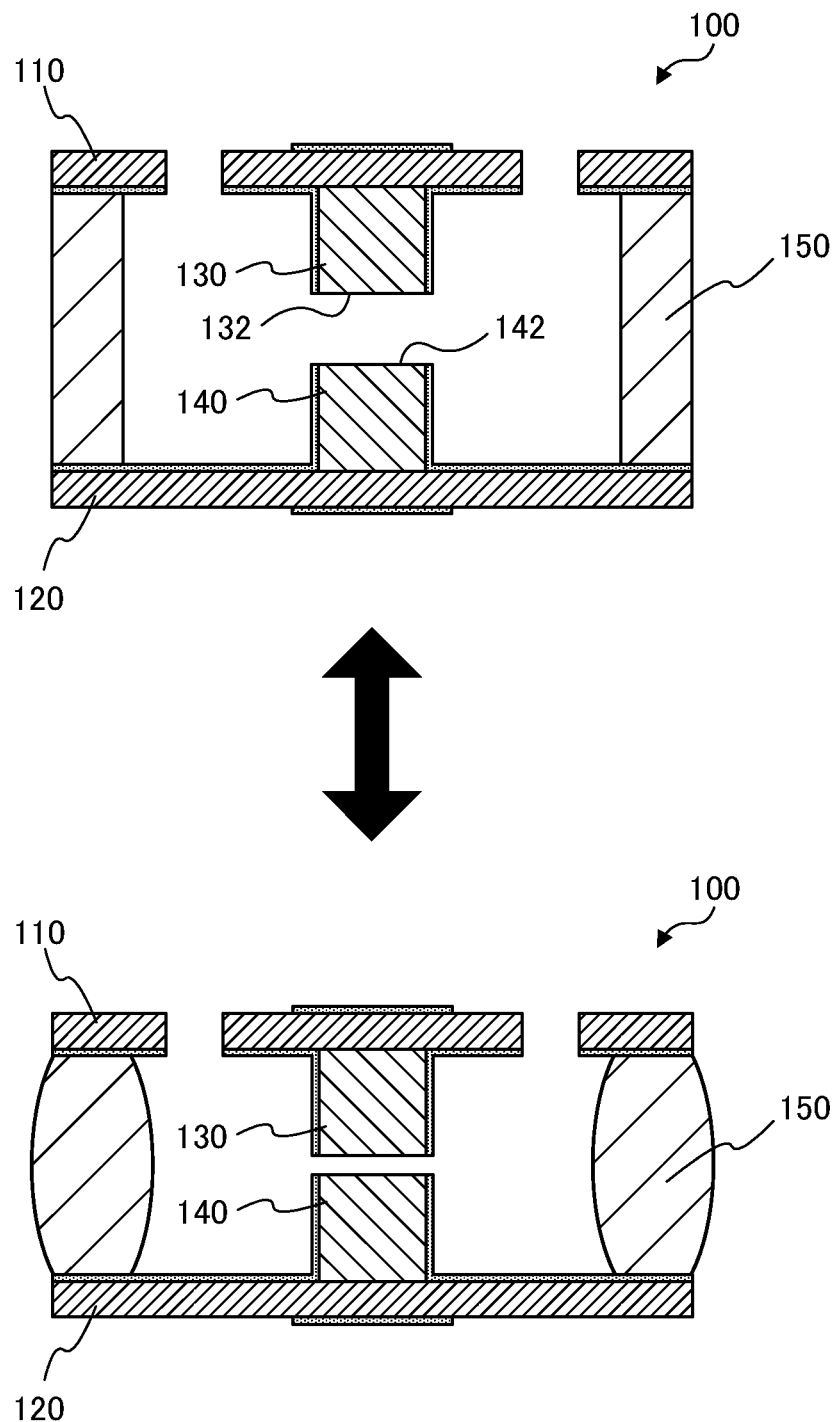
FIG. 5 is a sectional view of the detection device according to Embodiment 1 in which the distance between an emission surface and an incidence surface can be changed.

The material of sealing part 150 is not limited as long as sealing part 150 is not influenced by the object. Examples of the material of sealing part 150 include resins, rubber, and metals. From the viewpoint of adjustability of the distance between emission surface 132 and incidence surface 142, sealing part 150 is preferably composed of an elastic body. When sealing part 150 is provided with elasticity, the distance between emission surface 132 and incidence surface 142 can be adjusted as illustrated in FIG. 5, and the distance between first waveguide path 130 and second waveguide path 140 can be changed. In addition, reaction can be facilitated by agitating the fluid housed in detection device 100. By conducting measurement multiple times with variations of the distance between emission surface 132 and incidence surface 142, the difference of the object in absorption of terahertz waves can be determined. Even in the case where the material of sealing part 150 is a resin or a metal, the effect identical to that of sealing part 150 composed of an elastic body can be expected by forming sealing part 150 with a plurality of mutually slidable members, or by providing sealing part 150 with an accordion structure.

(Usage of Detection Device)

Next, a usage of detection device 100 is described.

Figure 6:
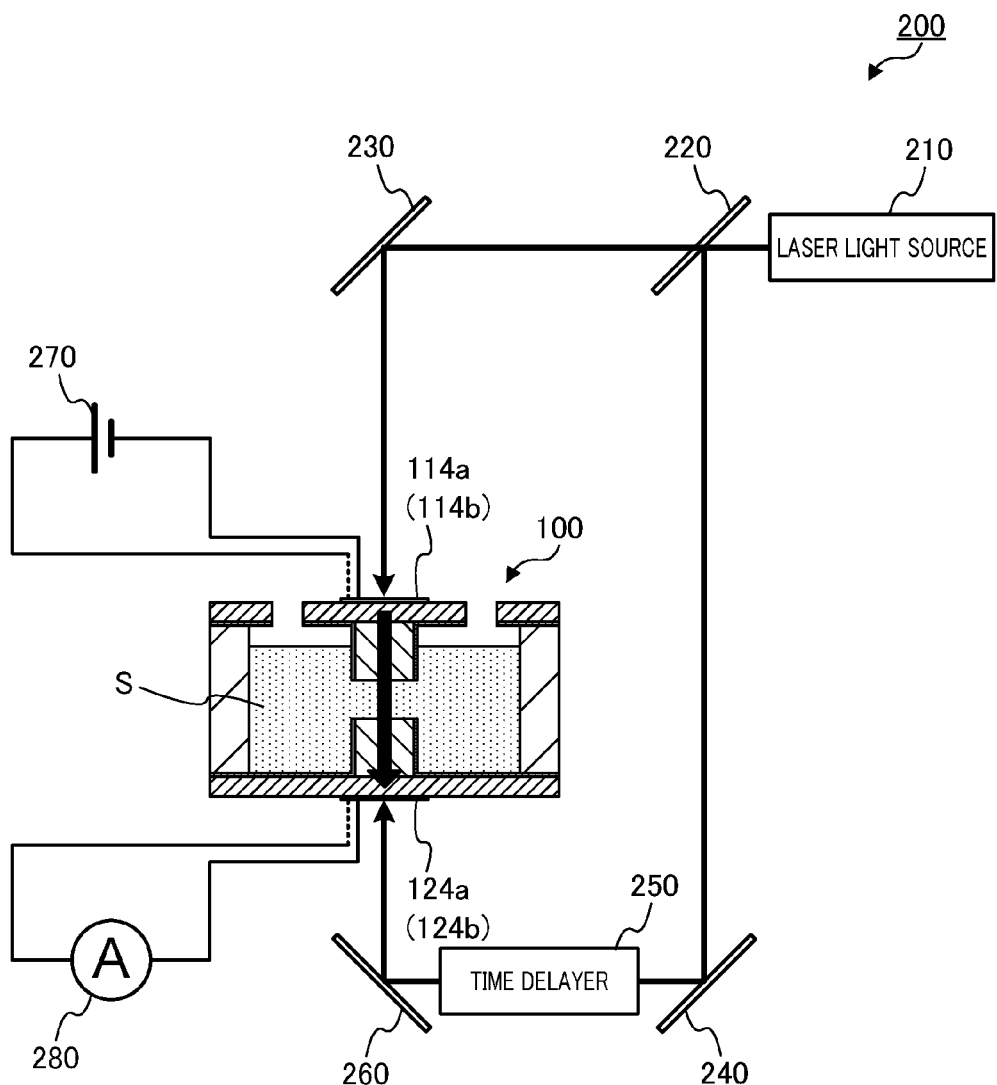
FIG. 6 is a schematic view illustrating a configuration of the detection apparatus according to Embodiment 1.

FIG. 6 illustrates a configuration of detection apparatus 200 for acquiring information of an object with use of detection device 100 according to the present embodiment. As illustrated in FIG. 6, detection apparatus 200 includes laser light source 210, beam splitter 220, mirrors 230, 240 and 260, time delayer 250, power source 270, ammeter 280 and detection device 100. Object (sample) S is housed in the internal space of detection device 100.

Laser light source 210 emits short-pulse laser light (for example, femtosecond pulse laser light). The light flux of pulse laser light is divided by beam splitter 220 into two light fluxes (pump light and probe light). The pump light is reflected by mirror 230, and reaches terahertz wave generation element 110 of detection device 100. Each of electrode films 114a and 114b of terahertz wave generation element 110 is connected with power source 270, and a predetermined voltage is applied across electrode films 114a and 114b. When pump light is applied to the gap between electrode films 114a and 114b in the above-mentioned state, pulsed terahertz waves are generated. The terahertz waves travel in first waveguide path 130 and are emitted from emission surface 132. Then, terahertz waves pass through an object (sample) S between emission surface 132 and incidence surface 142, and become terahertz waves containing information of object S.

The terahertz waves having passed through object S enter second waveguide path 140 from incidence surface 142, travel in second waveguide path 140, and reach terahertz wave detection element 120. On the other hand, the probe light passes through time delayer 250 after being reflected by mirror 240, and reaches terahertz wave detection element 120 of detection device 100 after being reflected by mirror 260. Each of electrode films 124a and 124b of terahertz wave detection element 120 is connected with ammeter 280. When terahertz waves reach terahertz wave detection element 120 at the time of application of the probe light to the gap between electrode films 124a and 124b, a current flows between electrode films 124a and 124b for a period corresponding to the pulse time width of the probe light and the carrier lifetime in photoconductive substrate 122. The value of the current corresponds to the value of the amplitude of the electric field of the terahertz waves having reached terahertz wave detection element 120. In addition, with use of time delayer 250, the timing of arrival of terahertz waves at the terahertz waves detection device 120 and the timing of arrival of the probe light at terahertz wave detection element 120 can be shifted from each other. Accordingly, the waveform of pulsed terahertz waves can be acquired by measuring the current with use of ammeter 280. The spectrum of the terahertz waves having passed through object S can be obtained by Fourier transform of the waveform of the terahertz waves. For example, the absorption spectrum of object S to the terahertz waves can be obtained by acquiring the spectrum of the terahertz waves of the state where object S is housed in the internal space of detection device 100 and the state where object S is not housed in the internal space of detection device 100, and calculating the ratio of the acquired the spectrums.

(Manufacturing Method of Detection Device)

The manufacturing method of detection device 100 according to the present embodiment is not limited. For example, detection device 100 is manufactured through the procedure illustrated in FIG. 7.

Figure 7A:
FIGS. 7A to 7F are sectional views illustrating a manufacturing method of the detection device according to Embodiment 1.
Figure 7B:
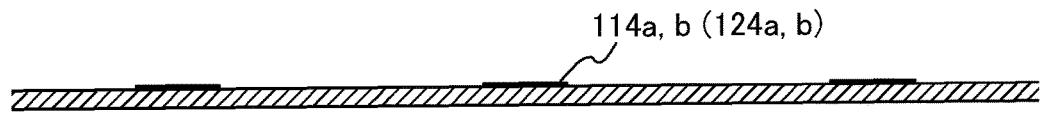
Figure 7C:
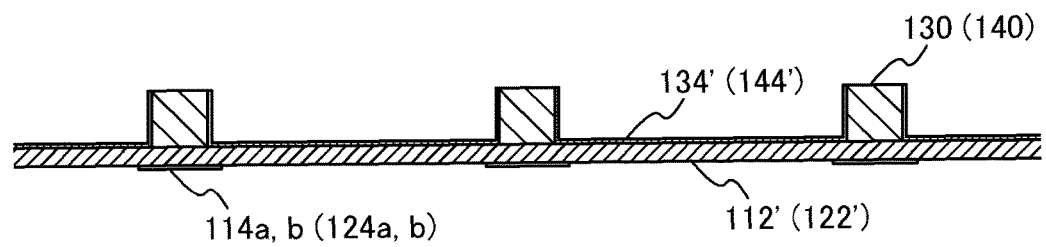

First, as illustrated in FIG. 7A, photoconductive substrate 112' in the form of a wafer is prepared. Next, as illustrated in FIG. 7B, a plurality of pairs of electrode films 114a and 114b are formed on one surface of photoconductive substrate 112'. The formation method of electrode films 114a and 114b is not limited. For example, electrode films 114a and 114b are formed by photolithography. Next, as illustrated in FIG. 7C, a plurality of first waveguide paths 130 are formed on the other surface of photoconductive substrate 112'. The formation method of first waveguide path 130 is not limited. For example, first waveguide path 130 is made of a resin material, and is formed by imprint molding. Thereafter, metal film 134 is formed on the side surface of first waveguide path 130 as necessary.

Through the above-mentioned steps, a plurality of the combinations of terahertz wave generation element 110 and first waveguide path 130 are formed on one photoconductive substrate 112'. In addition, through similar procedure, a plurality of the combinations of terahertz wave detection element 120 and second waveguide path 140 are formed on one photoconductive substrate 122'. Thereafter, through holes 116a and 116b are also formed in a region around terahertz wave generation element 110 in photoconductive substrate 112' on which a plurality of the combinations of terahertz wave generation element 110 and first waveguide path 130 are formed.

Figure 7D:
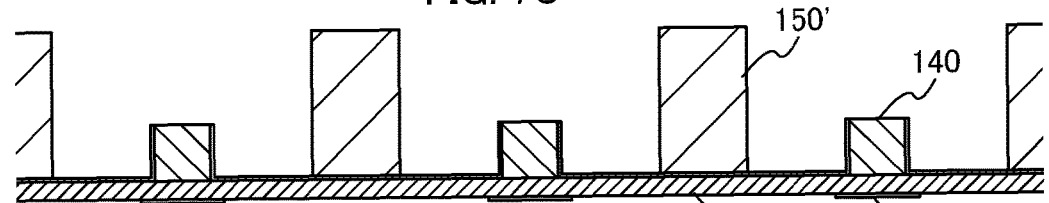
Figure 7E:
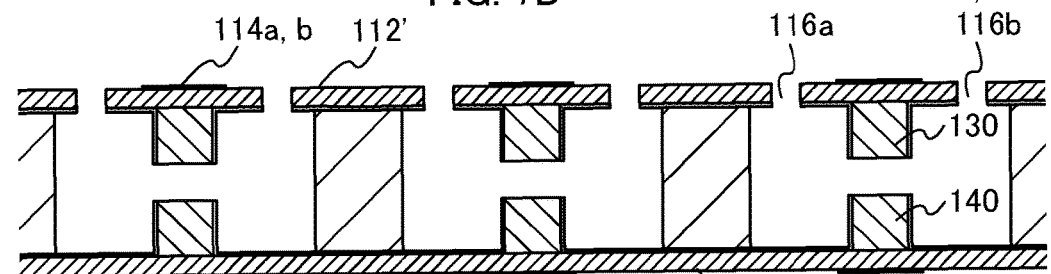

Next, as illustrated in FIG. 7D, sealing sheet 150' provided with a plurality of through holes is disposed and fixed (bonded) on photoconductive substrate 122' on which terahertz wave detection elements 120 and second waveguide path 140 are formed (or photoconductive substrate 112' on which terahertz wave generation elements 110 and first waveguide paths 130 are formed). Next, as illustrated in FIG. 7E, photoconductive substrate 112' on which terahertz wave generation elements 110 and first waveguide paths 130 are formed (or photoconductive substrate 122' on which terahertz wave detection elements 120 and second waveguide paths 140 are formed) is disposed and fixed (bonded) on sealing sheet 150'. In this manner, a laminated body including terahertz wave generation elements 110, terahertz wave detection elements 120, first waveguide paths 130 and second waveguide paths 140 is obtained. In this laminated body, first waveguide path 130 and second waveguide path 140 are housed in the through hole of sealing sheet 150'.

Figure 7F:
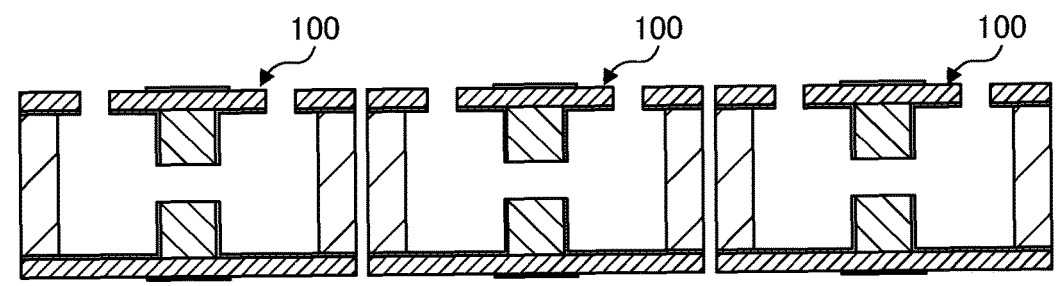

Finally, as illustrated in FIG. 7F, the laminated body is cut at a position between each through hole of sealing sheet 150', and thus a plurality of detection devices can be obtained.

(Effect)

As described above, in detection device 100 according to the present embodiment, a large space communicated with the space between emission surface 132 and incidence surface 142 is provided around first waveguide path 130 and second waveguide path 140. With this configuration, an object can be easily installed in the space between emission surface 132 and incidence surface 142 without increasing the size of detection device 100. In addition, a reaction of an object with another material can be easily caused in detection device 100.

While each of terahertz wave generation element 110 and terahertz wave detection element 120 is composed of a photoconductive antenna in the present embodiment, the type of terahertz wave generation element 110 and terahertz wave detection element 120 is not limited to a photoconductive antenna as described above. The means for generating terahertz waves and the means for detecting the terahertz waves may be appropriately changed when terahertz wave generation element 110 and terahertz wave detection element 120 are composed of other elements.

While two through holes 116a and 116b are formed in terahertz wave generation element 110 (photoconductive substrate 112) in the present embodiment, the number and position of through holes for housing an object is not limited. For example, one or a plurality of the through holes for housing an object may be provided. In addition, the position of the through hole for housing an object is not limited as long as the through hole is communicated with the space surrounded by terahertz wave generation element 110 (photoconductive substrate 112), terahertz wave detection element 120 (photoconductive substrate 122) and sealing part 150. To be more specific, the through hole may be formed in terahertz wave detection element 120 (photoconductive substrate 122) or sealing part 150.

[Embodiment 2]

A detection device according to Embodiment 2 is different from the detection device according to Embodiment 1 in that, for example, each of the terahertz wave generation element and the terahertz wave detection element has a plurality of pairs of electrode films. In view of this, the same components as those of detection device 100 according to Embodiment 1 are denoted by the same reference numerals, and the descriptions thereof are omitted.

Figure 8A:
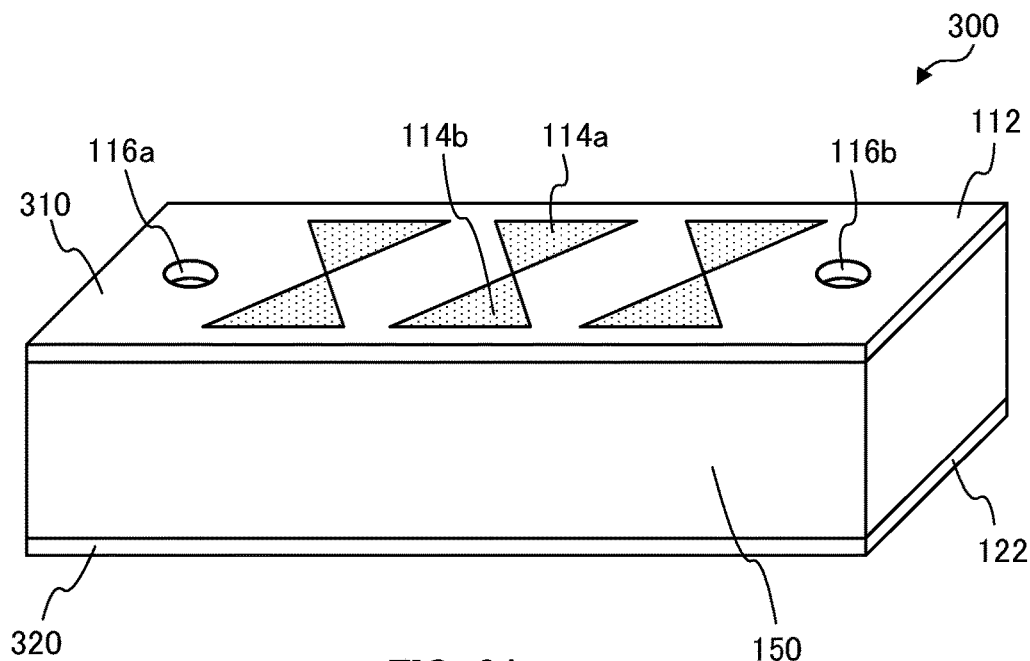
FIG. 8A is a perspective view of the detection device according to Embodiment 2.
Figure 8B:
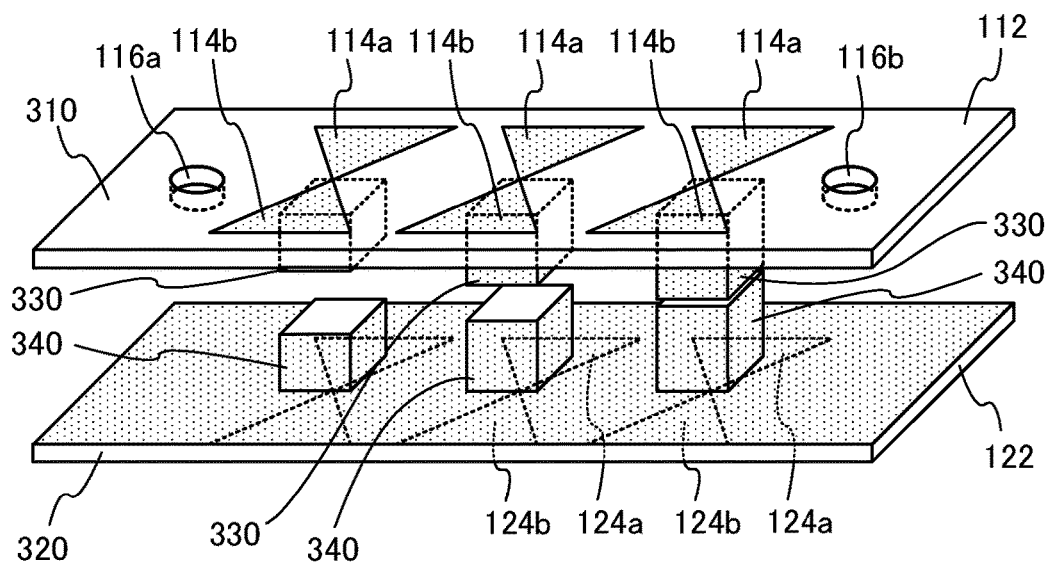
FIG. 8B is a perspective view of the detection device according to Embodiment 2 in which a sealing part is omitted.

FIG. 8A is a perspective view of detection device 300 according to Embodiment 2 of the present invention, and FIG. 8B is a perspective view of detection device 300 in which sealing part 150 is omitted.

As illustrated in FIG. 8, detection device 300 includes terahertz wave generation element 310, terahertz wave detection element 320, three first waveguide paths 330, three second waveguide paths 340 and sealing part 150.

Terahertz wave generation element 310 is a photoconductive antenna including photoconductive substrate 112, and three pairs of electrode films 114a and 114b disposed on photoconductive substrate 112. Likewise, terahertz wave detection element 320 is a photoconductive antenna including photoconductive substrate 122, and three pairs of electrode films 124a and 124b disposed on photoconductive substrate 122.

Three first waveguide paths 330 are respectively disposed on the rear side of the gaps of the three pairs of electrode films 114a and 114b of terahertz wave generation element 310. Likewise, three second waveguide paths 340 are respectively disposed on the rear side of the gaps of the three pairs of electrode films 124a and 124b of terahertz wave detection element 320. Emission surface 132 of each first waveguide path 330 faces incidence surface 142 of corresponding second waveguide path 340 with a space therebetween. That is, in detection device 300 of the present embodiment, three sets of a combination of a pair of electrode films 114a and 114b, one first waveguide path 330, one second waveguide path 340 and a pair of electrode films 124a and 124b are formed.

The length of first waveguide path 330 (the height from terahertz wave generation element 310) and the length of second waveguide path 340 (the height from terahertz wave detection element 320) are different among the combinations of first waveguide path 330 and second waveguide path 340. Accordingly, the distance between emission surface 132 and incidence surface 142 is different among the combinations of first waveguide path 330 and second waveguide path 340. In the example illustrated in FIG. 8B, the lengths of first waveguide path 330 and second waveguide path 340 illustrated on the left side are small (the distance between emission surface 132 and incidence surface 142 is large), and the lengths of first waveguide path 330 and second waveguide path 340 illustrated on the right side are large (the distance between emission surface 132 and incidence surface 142 is small). It is to be noted that first waveguide paths 330 and second waveguide paths 340 have the same width.

In addition to the effect of detection device 100 of Embodiment 1, detection device 300 according to Embodiment 2 can perform measurement while changing the distance between emission surface 132 and incidence surface 142 for the same object by only changing the position for irradiation of the pump light and the probe light.

Figure 9:
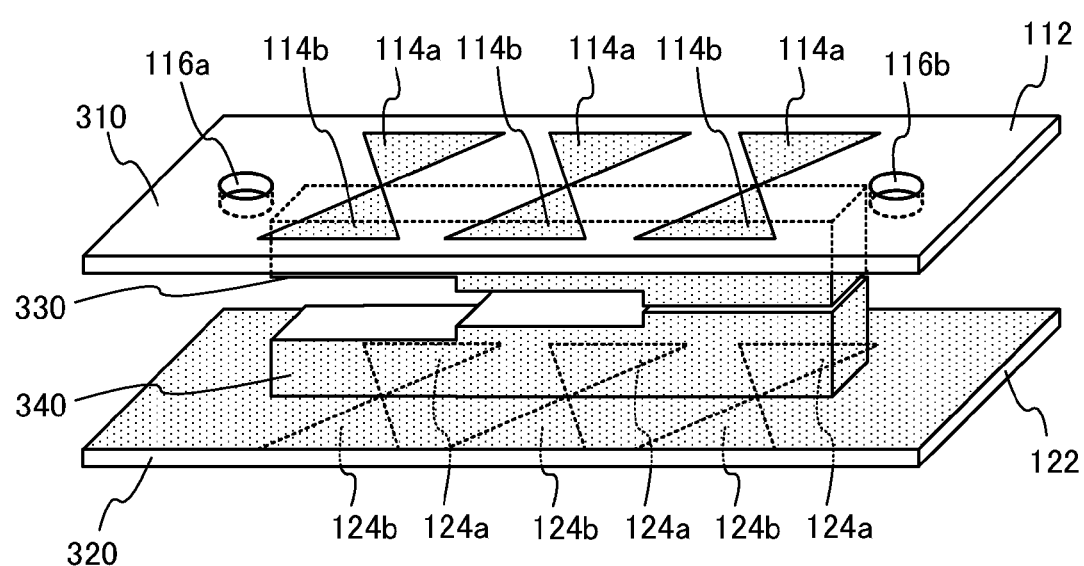
FIG. 9 is a perspective view of a modification of the detection device according to Embodiment 2 in which a sealing part is omitted.

While three first waveguide paths 330 are separately formed, and three second waveguide paths 340 are separately formed in the present embodiment, three first waveguide paths 330 may be integrally formed, and, three second waveguide paths 340 may be integrally formed as illustrated in FIG. 9.

[Embodiment 3]

A detection device according to Embodiment 3 is different from the detection device according to Embodiment 2 in that, for example, the widths of a plurality of first waveguide paths and the widths of a plurality of second waveguide paths are different from each other. In view of this, the same components as those of detection device 100 according to Embodiment 1 or detection device 300 according to Embodiment 2 are denoted by the same reference numerals, and the descriptions thereof are omitted.

Figure 10A:
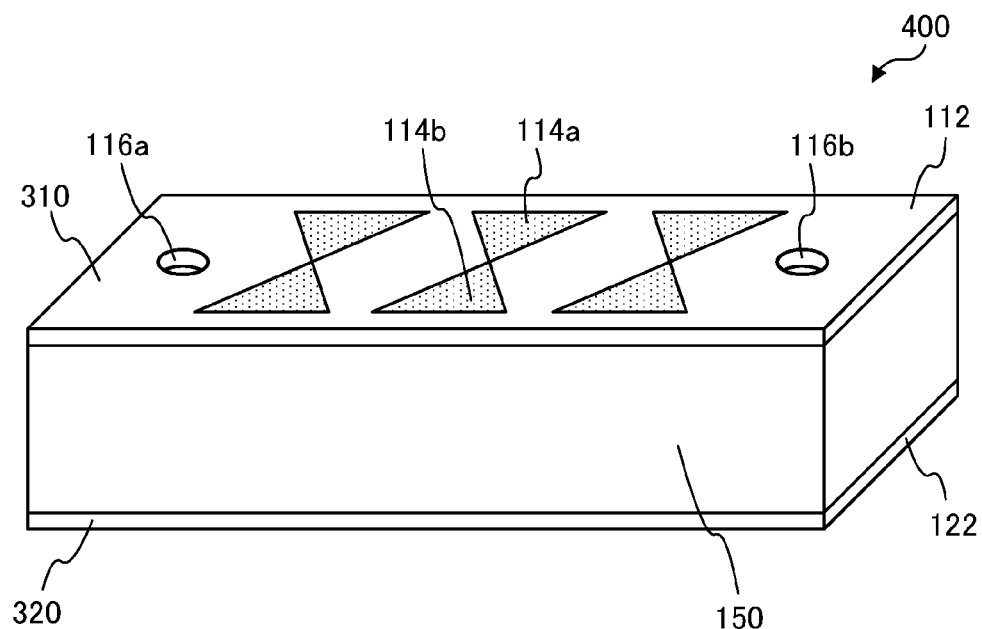
FIG. 10A is a perspective view of a detection device according to Embodiment 3.
Figure 10B:
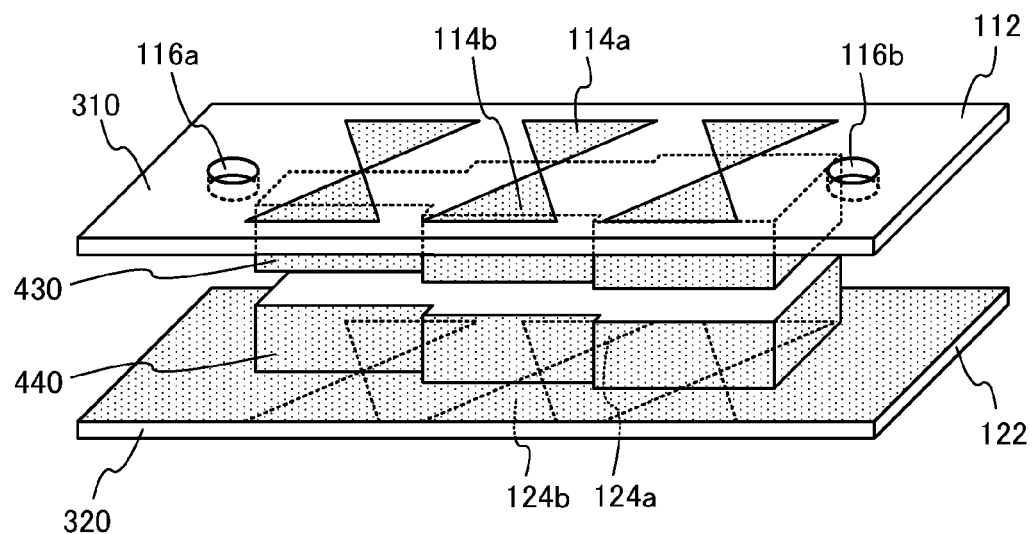
FIG. 10B is a perspective view of the detection device according to Embodiment 3 in which a sealing part is omitted.

FIG. 10A is a perspective view of detection device 400 according to Embodiment 3 of the present invention, and FIG. 10B is a perspective view of detection device 400 in which sealing part 150 is omitted.

As illustrated in FIG. 10, detection device 400 includes terahertz wave generation element 310, terahertz wave detection element 320, three first waveguide paths 430, three second waveguide paths 440 and sealing part 150.

Three first waveguide paths 430 are integrally formed and three second waveguide paths 440 are integrally formed. The width of first waveguide path 430 and the width second waveguide path 440 are different from each other among the combinations of first waveguide path 430 and second waveguide path 440. In the example illustrated in FIG. 10B, the widths of first waveguide path 430 and second waveguide path 440 illustrated on the left side are small, and the widths of first waveguide path 430 and second waveguide path 440 illustrated on the right side are large. It is to be noted that first waveguide path 430 and second waveguide path 440 have the same distance therebetween.

In addition to the effect of detection device 100 of Embodiment 1, detection device 400 according to Embodiment 3 can perform measurement while changing the wavelength of the applied terahertz waves for the same object by only changing the position for irradiation of the pump light and the probe light.

Figure 11:
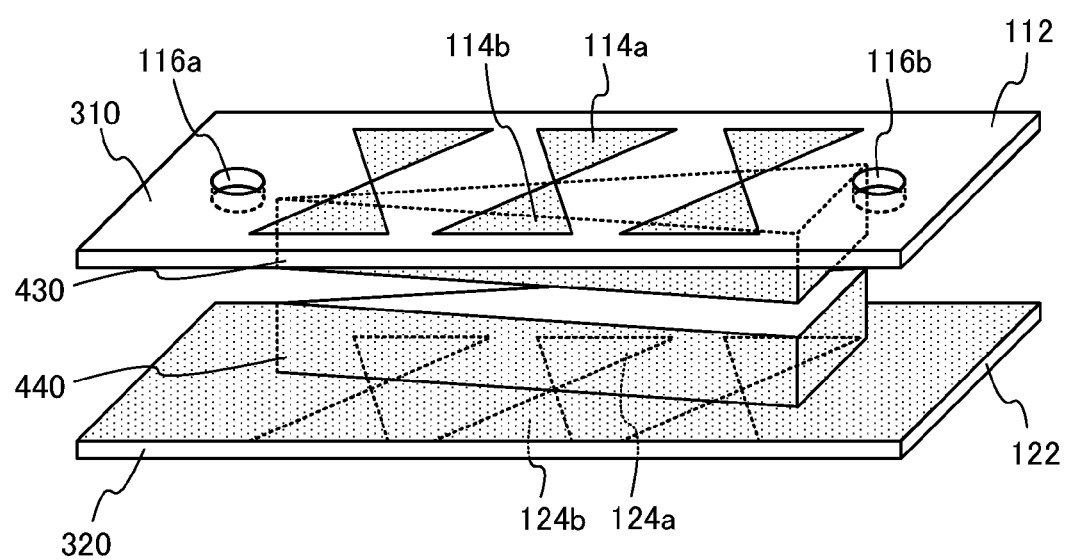
FIG. 11 is a perspective view of a modification of the detection device according to Embodiment 3 in which the sealing part is omitted.

While the widths of integrally formed three first waveguide paths 430 and integrally formed three second waveguide paths 440 are discontinuously changed in the present embodiment, the widths of integrally formed three first waveguide paths 430 and integrally formed three second waveguide paths 440 may be continuously (successively) changed as illustrated in FIG. 11.

While three pairs of electrode films 114a and 114b are disposed for three first waveguide paths 330 and 430 and three pairs of electrode films 124a and 124b are disposed for three second waveguide paths 340 and 440 in Embodiment 2 and Embodiment 3, a pair of slidable electrode films may be disposed for a plurality of first waveguide paths 330 and 430 or second waveguide paths 340 and 440 instead of disposing a corresponding number of pairs of electrode films.

While each of the transmission path (first transmission path) disposed on the rear side of terahertz wave generation element 110 and the transmission path (second transmission path) disposed on the rear side of terahertz wave detection element 120 is composed of a waveguide path in the Embodiments, the type of the first transmission path and the second transmission path is not limited to this. For example, each of the first transmission path and the second transmission path may also be a waveguide pipe or a transmission line.

This application is entitled to and claims the benefit of Japanese Patent Application No. 2014-100320 filed on May 14, 2014, the disclosure each of which including the specification, drawings and abstract is incorporated herein by reference in its entirety.

INDUSTRIAL APPLICABILITY

The detection device according to the embodiments of the present invention is suitable for food inspection and the like, for example.

REFERENCE SIGNS LIST

10 Detection device
12a, 12b Metal plate
14a, 14b Polystyrene plate
16a, 16b Photoconductive antenna
18 Space
100, 300, 400 Detection device
110, 310 Terahertz wave generation element
112, 112' Photoconductive substrate
114a, 114b Electrode film
116a, 116b Through hole
120, 320 Terahertz wave detection element
122, 122' Photoconductive substrate
124a, 124b Electrode film
130, 330, 430 First waveguide path
132 Emission surface
134, 144 Metal film
136, 146 Base
140, 340, 440 Second waveguide path
142 Incidence surface
150 Sealing part
150' Sealing sheet
200 Detection device
210 Laser light source
220 Beam splitter
230, 240, 260 Mirror
250 Time delayer
270 Power source
280 Ammeter
S Object (Sample)

The invention claimed is:

1. A detection device for acquiring information of an object by detecting a state of terahertz waves having passed through the object, the detection device comprising:
   a terahertz wave generation element;
   a terahertz wave detection element disposed to face the terahertz wave generation element;

a first transmission path disposed on the terahertz wave generation element to protrude from the terahertz wave generation element toward the terahertz wave detection element;
a second transmission path disposed on the terahertz wave detection element to protrude from the terahertz wave detection element toward the terahertz wave generation element; and
a sealing part disposed between the terahertz wave generation element and the terahertz wave detection element to surround the first transmission path and the second transmission path, the sealing part being separated from the first transmission path and the second transmission path, wherein:
the first transmission path includes an emission surface which emits terahertz waves generated at the terahertz wave generation element, the emission surface being disposed at an end of the first transmission path;
the second transmission path includes an incidence surface on which the terahertz waves emitted from the emission surface are incident, the incidence surface being disposed at an end of the second transmission path to face the emission surface, the incidence surface being separated from the emission surface; and
a space between the emission surface and the incidence surface is communicated with a space between the first transmission path and the sealing part and a space between the second transmission path and the sealing part.

2. The detection device according to claim 1, wherein the terahertz wave generation element, the terahertz wave detection element or the sealing part is provided with a through hole communicated with a space surrounded by the terahertz wave generation element, the terahertz wave detection element and the sealing part.

3. The detection device according to claim 1, wherein each of the terahertz wave generation element and the terahertz wave detection element is a photoconductive antenna including a photoconductive substrate and at least one pair of electrode films disposed on the photoconductive substrate.

4. The detection device according to claim 3, wherein the photoconductive antenna includes a plurality of pairs of electrode films.

5. The detection device according to claim 4, wherein:
in a cross-section parallel to the emission surface of the first transmission path, the first transmission path has a width which is discontinuously changed; and
in a cross-section parallel to the incidence surface of the second transmission path, the second transmission path has a width which is discontinuously changed.

6. The detection device according to claim 4, wherein:
in a cross-section parallel to the emission surface of the first transmission path, the first transmission path has a width which is continuously changed; and
in a cross-section parallel to the incidence surface of the second transmission path, the second transmission path has a width which is continuously changed.

7. The detection device according to claim 1, wherein the sealing part is composed of an elastic body.

8. The detection device according to claim 1, wherein a distance between the emission surface and the incidence surface is 10 to 100 µm.

9. The detection device according to claim 1, wherein each of the first transmission path and the second transmission path has a length of 10 µm or greater.

10. The detection device according to claim 1, wherein each of the first transmission path and the second transmission path is a waveguide path, a waveguide pipe or a transmission line.

11. A method of manufacturing the detection device according claim 1, the method comprising:
forming a plurality of pairs of first electrode films on a first surface of a first photoconductive substrate;
forming a plurality of pairs of second electrode films on a first surface of a second photoconductive substrate;
forming a plurality of first transmission paths on a second surface of the first photoconductive substrate;
forming a plurality of second transmission paths on a second surface of the second photoconductive substrate;
producing a laminated body by disposing a sealing sheet including a plurality of through holes for housing the first transmission path and the second transmission path at a position between the second surface of the first photoconductive substrate and the second surface of the second photoconductive substrate, and by fixing the first photoconductive substrate, the sealing sheet and the second photoconductive substrate; and
obtaining a plurality of detection devices by cutting the laminated body at a position between the through holes.

12. The method according to claim 11, wherein the first transmission path and the second transmission path are formed by imprint molding.

13. The detection device according to claim 4, wherein:
the first transmission path includes, as the emission surface, a plurality of emission surfaces provided at positions corresponding to the pairs of electrode films; and
the second transmission path includes, as the incidence surface, a plurality of incidence surfaces provided at positions corresponding to the pairs of electrode films.

14. The detection device according to claim 13, wherein the emission surfaces of the first transmission path and the incidence surfaces of the second transmission path include two or more pairs of the emission surface and the incidence surface which are different in a distance between the emission surface and the incidence surface corresponding to each other.

15. The detection device according to claim 4, wherein:
the first transmission path includes a plurality of transmission paths provided at respective positions corresponding to the pairs of electrode films; and
the second transmission path includes a plurality of transmission paths provided at respective positions corresponding to the pairs of electrode films.

16. The detection device according to claim 15, wherein the emission surfaces of the transmission paths of the first transmission path, and the incidence surfaces of the transmission paths of the second transmission path include two or more pairs of the emission surface and the incidence surface which are different in a distance between the emission surface and the incidence surface corresponding to each other.

17. A measurement method comprising:
emitting terahertz wave from the emission surface of the first transmission path, in a state where a space between the emission surface and the incidence surface, a space between the first transmission path and the sealing part, and a space between the second transmission path and the sealing part are filled with a measurement object in the detection device according to claim 1;

detecting a state of the terahertz wave which passes through the object after the emission and enters the incident surface of the second transmission path; and obtaining information of the object according to the detected state of the terahertz wave.

18. The measurement method according to claim 17 wherein the object is fluid.

19. The measurement method according to claim 17 which further comprises:

emitting terahertz wave from the emission surface of the first transmission path in a state where the spaces are not filled with a measurement object in the detection device according to claim 1;

detecting a state of the terahertz wave which enters the incident surface of the second transmission path without passing through the measurement object; and comparing both of the detected states of terahertz waves each other.

\* \* \* \* \*